United States Patent
Dosmann

(10) Patent No.: US 8,226,904 B2
(45) Date of Patent: Jul. 24, 2012

(54) OPTICAL FORMAT WITH PLATFORM-AND-WELL CONSTRUCTION

(75) Inventor: Andrew J. Dosmann, Granger, IN (US)

(73) Assignee: Bayer Healthcare LLC, Tarrytown, NY (US)

( * ) Notice: Subject to any disclaimer, the term of this patent is extended or adjusted under 35 U.S.C. 154(b) by 765 days.

(21) Appl. No.: 10/576,993

(22) PCT Filed: Oct. 29, 2004

(86) PCT No.: PCT/US2004/036330
§ 371 (c)(1),
(2), (4) Date: Apr. 25, 2006

(87) PCT Pub. No.: WO2005/043134
PCT Pub. Date: May 12, 2005

(65) Prior Publication Data
US 2007/0031960 A1    Feb. 8, 2007

Related U.S. Application Data

(60) Provisional application No. 60/515,338, filed on Oct. 30, 2003.

(51) Int. Cl.
*G01N 33/00* (2006.01)
(52) U.S. Cl. ............... 422/402; 422/82.05; 422/414; 436/104; 436/165; 436/531; 436/86; 436/164
(58) Field of Classification Search ............... 422/55, 422/58, 68.1
See application file for complete search history.

(56) References Cited

U.S. PATENT DOCUMENTS

| | | | | |
|---|---|---|---|---|
| 4,088,448 A | * | 5/1978 | Lilja et al. | 422/102 |
| 4,756,884 A | | 7/1988 | Hillman et al. | 422/73 |
| 5,035,494 A | | 7/1991 | Foldenauer | 350/536 |
| 5,072,595 A | | 12/1991 | Barbier | 62/129 |
| 5,148,596 A | | 9/1992 | Zahn | 29/842 |
| 5,337,468 A | | 8/1994 | Zahn | 29/842 |
| 5,371,020 A | | 12/1994 | Frischauf | 436/165 |
| 5,525,518 A | | 6/1996 | Lundsgaard et al. | 436/68 |
| 5,564,419 A | | 10/1996 | Lundsgaard et al. | 600/317 |
| 5,616,053 A | | 4/1997 | Bogursky et al. | 439/590 |
| 5,620,086 A | | 4/1997 | Bianca et al. | 200/542 |
| 5,706,952 A | | 1/1998 | Bianca et al. | 206/713 |
| 5,725,392 A | | 3/1998 | Bianca et al. | 439/590 |
| 5,749,458 A | | 5/1998 | Bianca et al. | 200/541 |
| 5,938,996 A | | 8/1999 | Bianca et al. | 264/145 |
| 5,957,725 A | | 9/1999 | Bianca et al. | 439/590 |
| 5,957,739 A | | 9/1999 | Bianca et al. | 439/885 |
| 5,967,841 A | | 10/1999 | Bianca et al. | 439/590 |
| 6,123,820 A | | 9/2000 | Bergkuist et al. | |
| 6,202,853 B1 | | 3/2001 | Bianca et al. | 206/713 |

(Continued)

FOREIGN PATENT DOCUMENTS

EP    0418993 A2    3/1991

(Continued)

*Primary Examiner* — Sally Sakelaris
(74) *Attorney, Agent, or Firm* — Nixon Peabody LLP

(57) ABSTRACT

Formats for optical analysis of fluid samples are provided with platforms and wells for contacting fluid samples and bringing reagents in contact with fluid samples. Formats may be made in opposing platform-and-well constructions, allowing a platform protruding from one format member to enter a well contained within an opposing format member. A sample fill nose accepts sample fluid from a sample collection opening and transports the sample fluid through the format.

22 Claims, 3 Drawing Sheets

U.S. PATENT DOCUMENTS

| | | |
|---|---|---|
| 6,391,541 B1 | 5/2002 | Petersen et al. ............... 435/5 |
| 2002/0061260 A1* | 5/2002 | Husar ........................... 422/100 |
| 2002/0079218 A1 | 6/2002 | Brenneman et al. ......... 204/400 |
| 2002/0145121 A1* | 10/2002 | Huhn et al. ................... 250/573 |

FOREIGN PATENT DOCUMENTS

| | | |
|---|---|---|
| EP | 0418993 B1 | 1/1996 |
| EP | 0753901 A2 | 1/1997 |
| EP | 0785709 A2 | 7/1997 |
| EP | 0843389 A2 | 5/1998 |
| EP | 0847112 A1 | 6/1998 |
| EP | 0872920 A2 | 10/1998 |
| EP | 0753901 B1 | 10/2000 |
| EP | 0847112 B1 | 3/2001 |
| EP | 0785709 B1 | 5/2001 |
| EP | 0695937 B1 | 5/2002 |
| EP | 1215479 A2 | 6/2002 |
| FR | 2 835 617 | 2/2002 |

* cited by examiner

OPTICAL FORMAT WITH PLATFORM-AND-WELL CONSTRUCTION

Cross-Reference To Related Application

This application claims priority to U.S. Provisional Application No. 60/515,338, filed on Oct. 30, 2003 which is incorporated by reference in its entirety.

FIELD OF THE INVENTION

The present invention relates generally to electrochemical analysis and more specifically to an optical format for fluid analysis.

BACKGROUND OF THE INVENTION

Optical testing of samples has become increasingly popular in recent years due to the speed, accuracy, and efficiency with which test results can be acquired through optical testing. Because of these benefits, optical testing is commonly used in medical applications such as glucose testing, with the sample fluid being blood. Generally, optical testing in medical applications involves allowing light to interact with a sample. In some applications, the sample may be combined with a reagent for testing. Optical testing may be accomplished using "formats," which allow for the collection of a sample, combination of the sample with a reagent, and optical testing of the sample.

Several problems arise in optical testing applications. A common problem with sample testing is the necessary sample size to allow reaction with a reagent and enable accurate testing. Many optical formats require sample sizes of 300 nl or greater. Further, optical formats often result in performance errors due to poor mechanical tolerances of the formats. When a reagent is used with an optical format, the reagent may be inconsistently placed within the format. For example, an improper amount of reagent or reagent placed in the wrong location may affect test accuracy. Formats resulting in improper control of sample volume—for example, deposition of an insufficient sample volume within a test area—decrease the accuracy of many prior art optical testing systems. Further, the costs of manufacturing optical formats can be high, and resulting formats are often larger than desired.

In order to increase the efficiency and accuracy of optical sample testing, it is desirable to provide an improved optical format.

SUMMARY OF THE INVENTION

According to one embodiment of the present invention, an optical format allows a very small sample volume to result in accurate optical testing.

According to some embodiments of the present invention, an optical format is provided which allows accurate optical testing of sample volumes of approximately 50 nl.

According to some embodiments of the present invention, an optical format consists of two pieces designed to join into a single format allowing accurate testing of small optical volumes.

According to some embodiments of the present invention, optical formats allow the consistent placing of reagent within the optical format.

According to some embodiments of the present invention, reagent placement is facilitated by the use of a mesa upon which a reagent is placed during manufacturing of the format.

According to some embodiments of the present invention, sample volume is metered to a required amount within an optical format before the sample is allowed to react with a reagent within the optical format.

According to some embodiments of the present invention, an optical format is manufactured using continuous web processing to enable high-speed production of optical formats at low cost.

Figure 1:
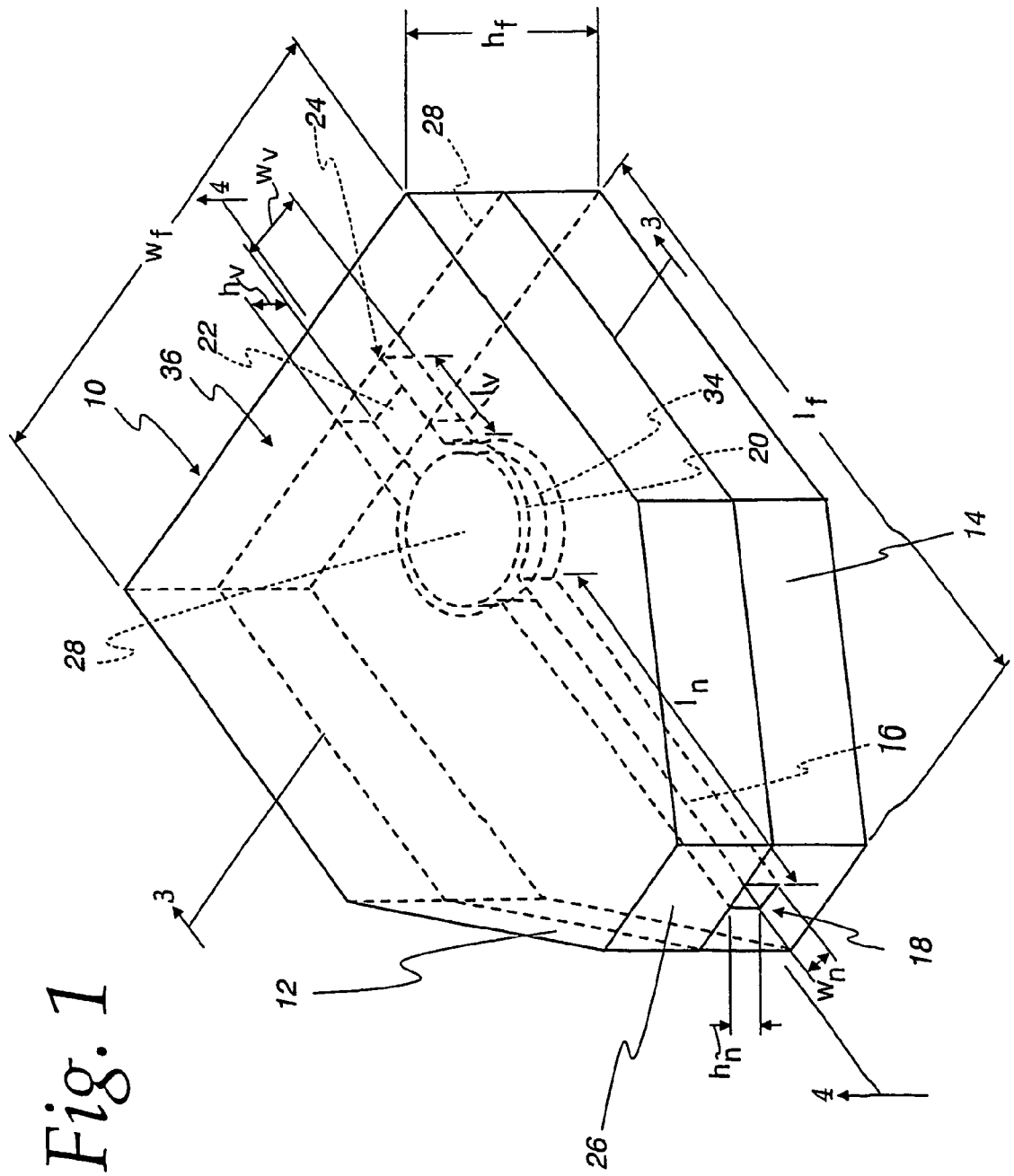
FIG. 1 is a perspective view of an optical format according to one embodiment of the present invention.

While the invention is susceptible to various modifications and alternative forms, specific embodiments are shown by way of example in the drawings and will be described in detail herein. However, it should be understood that the invention is not intended to be limited to the particular forms disclosed. Rather, the invention is to cover all modifications, equivalents, and alternatives falling within the spirit and scope of the invention as defined by the appended claims.

DETAILED DESCRIPTION OF THE ILLUSTRATED EMBODIMENTS

FIG. 1 shows an optical format 10 according to one embodiment of the present invention. The optical format 10 may be used in the collection and optical testing of samples, for example in medical testing applications such as glucose testing or testing of other analytes in biological fluid analysis. The optical format 10 may be created using a variety of fabrication techniques, such as micro-molding, coining, or UV replication processes, and may be constructed of such materials as polycarbonate, polystyrene, and polyester. Formats according to the present invention may be individually cut out of sheet material, cut into one- or two-dimensional arrays, or cut into a circular disc arrangement. Continuous web processing may be used to manufacture formats and format members according to the present invention, resulting in lower processing costs.

The optical format 10 comprises a first format member 12 and a second format member 14. Though the first and second format members 12 and 14 are discussed in relation to top and bottom directions as shown in FIG. 1, it is to be understood that these labels are for the purposes of discussion and that the features of optical formats according to the present invention may be alternatively oriented in space—for example, features discussed in combination with the first format member 12 may be placed on a lower format portion according to some embodiments of the present invention.

The second format member 14 shown in FIG. 1 is provided with a sample fill nose 16. The sample fill nose 16 provides for the collection of sample fluid from a sample collection opening 18 and transport of the sample fluid from the sample collection opening 18 to a well 20. The well 20 is connected to a vent 22 provided with a vent opening 24. In the embodiment shown in FIG. 1, the sample collection opening 18 is provided on a front face 26 of the optical format, and the vent opening 24 is provided on a back face 28 of the optical format. According to some embodiments of the present invention, sample collection openings and vent openings may be provided on other faces of optical formats, or at face interfaces of optical formats, as required by particular applications of the optical format.

According to some embodiments of the present invention, the sample fill nose 16 transports sample fluid from the sample collection opening 18 to the well 20 via capillary action. The sample fill nose 16 is preferably provided with dimensions such that the open volume of the sample fill nose 16 is approximately equal to the volume of sample fluid required for analysis within the well 20.

In an embodiment in which the sample fill nose 16 has a rectangular cross-section, the sample fill nose 16 has a height, $h_n$, a width, $w_n$, and a length, $l_n$. According to one embodiment of the present invention, the volume of sample preferred for testing within the well 20 is approximately 50 nl. In this embodiment, a sample fill nose 16 having a height $h_n$ of approximately 100 µm, a width $w_n$ of approximately 200 µm and a length, $l_n$, of approximately 2.4 mm is appropriate to fill the well 20 with the desired amount of sample fluid. Thus, the sample volume is appropriately metered by the sample fill nose 16 during sample collection. According to some embodiments of the present invention, it may be desirable to conduct testing with greater or lesser amounts of fluid, and the well 20 and the sample fill nose 16 may be sized to enable optimum fluid transport to the well 20. The dimensions of the format are dependent on the manufacturing process, but in general the maximum preferred sample volume of 1 µl limits the size of the format.

Figure 2:
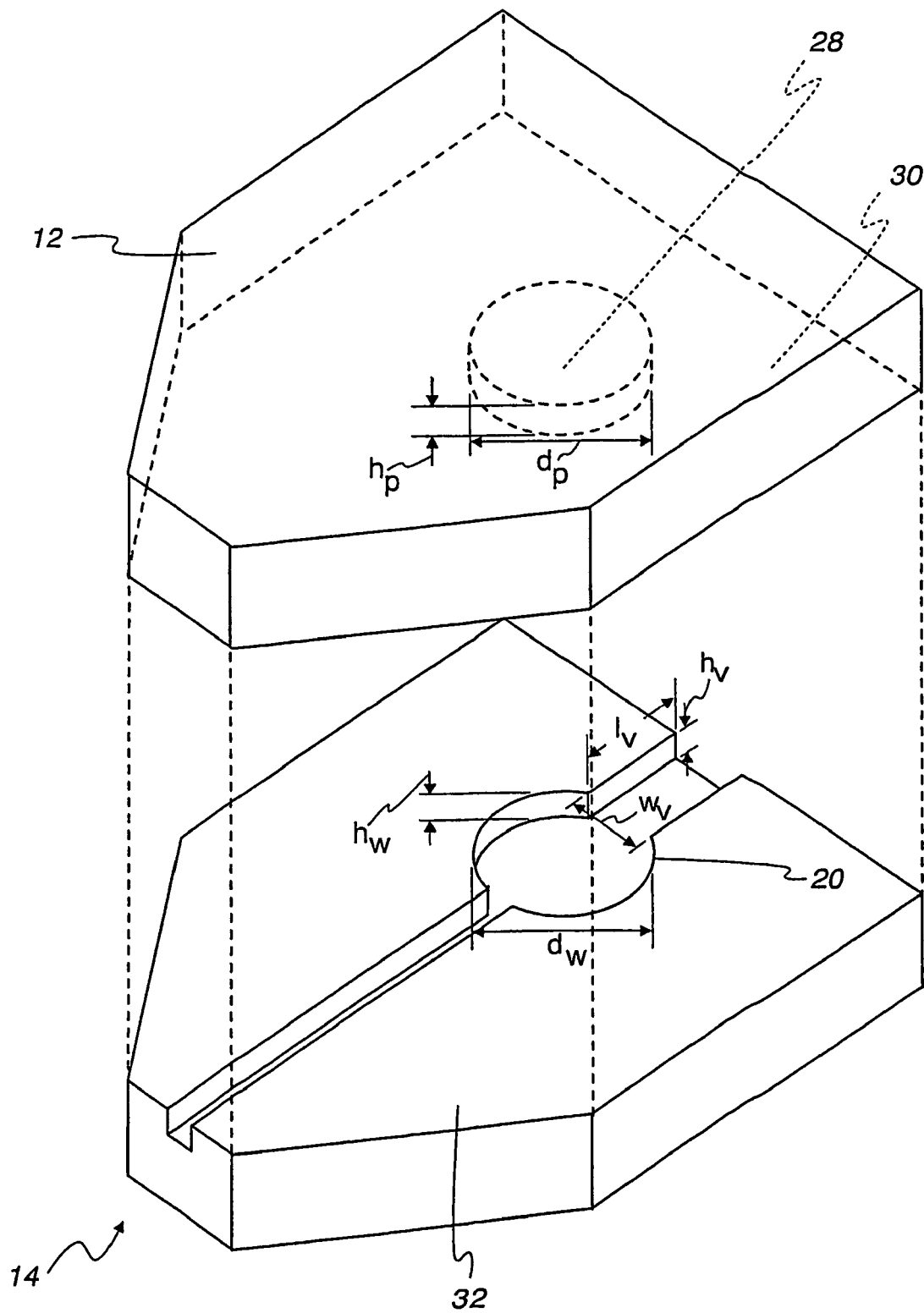
FIG. 2 is an exploded perspective view of an optical format according to one embodiment of the present invention.
Figure 3:
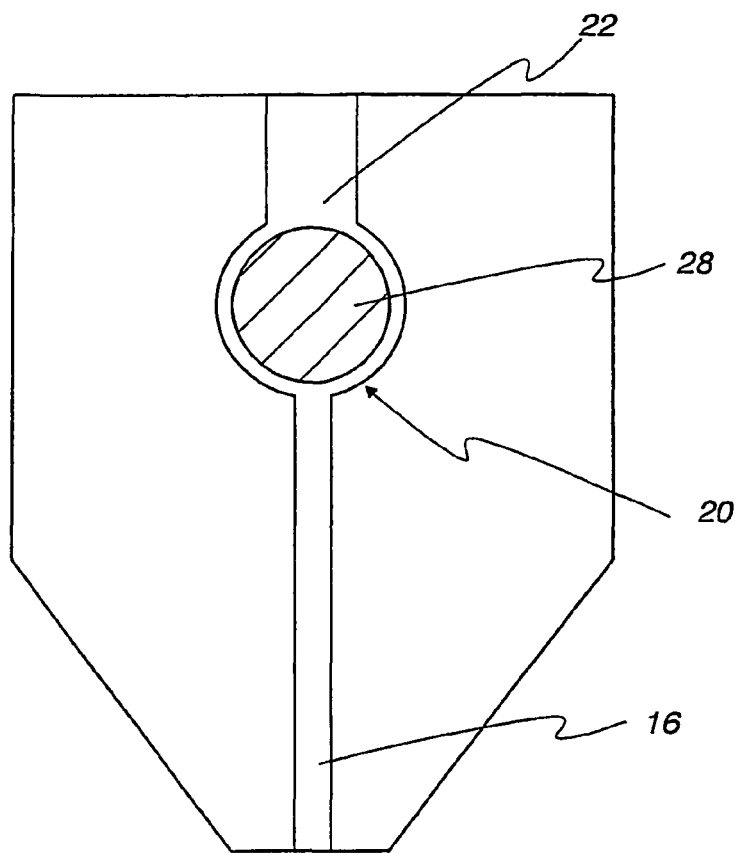
FIG. 3 is a top cross-sectional view along the line 3-3 of the optical format of FIG. 1.

According to some embodiments of the present invention, a platform 28 is provided on an optical format member. The platform 28 is raised from an inner surface 30 of one of the optical platform members, as shown in FIG. 2. FIGS. 1 and 2 show the platform 28 extending downwardly from the inner surface 30 of the first platform member 12, but it is to be understood that optical formats according to the present invention may employ platforms extending upwardly from a bottom platform member. In the embodiment shown in FIGS. 1 and 2, the platform 28 extends downwardly from the inner surface 30 of the first optical format member 12 and into the well 20 provided in the inner surface 32 of the second optical format member 14.

The platform 28 extends a height $h_p$ from the inner surface 30 of the first format member 12. The platform 28 may be a circular platform with a diameter $d_p$. According to one embodiment of the present invention, the height $h_p$ of the platform 28 is approximately 50 µm and the diameter $d_p$ of the platform 28 is approximately 1000 µm, but greater or lesser heights and diameters may be used in specific applications of the present invention. For example, heights ranging from about 25 µm to about 250 µm and diameters ranging from about 500 µm to about 2000 µm are preferred in some embodiments of the present invention.

Figure 4:
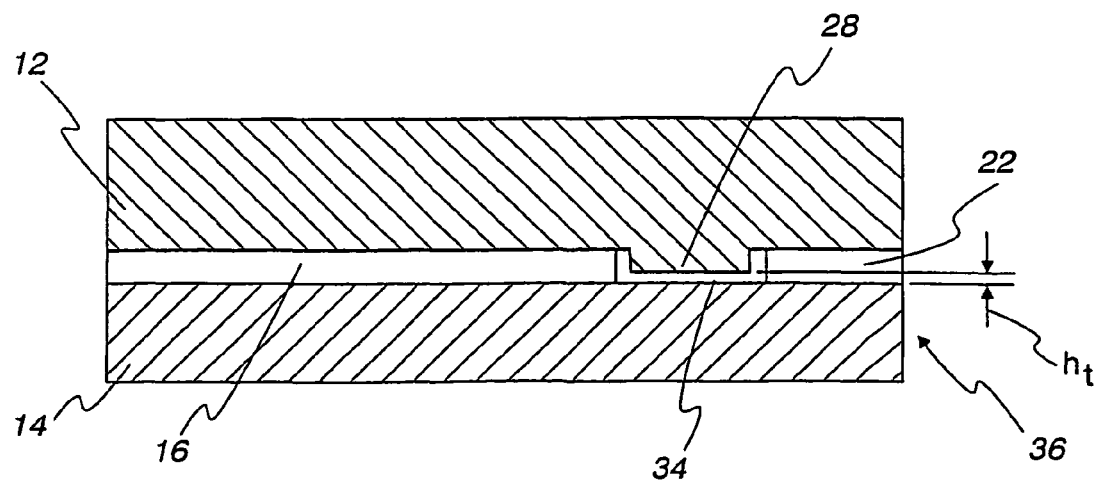
FIG. 4 is a side cross-sectional view along the line 4-4 of the optical format of FIG. 1.

For the platform 28 to enter the well 20, the well 20 is provided with a diameter, $d_w$, larger than the diameter $d_p$ of the platform 28. According to one embodiment of the present invention, the diameter $d_w$ of the well is approximately 1050 µm. Larger or smaller well diameters are possible. For example, well diameters ranging from about 550 µm to about 2050 µm are preferred in some embodiments of the present invention. Further, the well is provided with a depth $h_w$ that is deeper than the height $h_p$ of the platform 28, thereby forming a sample testing region 34, most easily seen in FIG. 4. According to one embodiment of the present invention, the sample testing region 34 has a height $h_t$ of approximately 50 µm. Larger or smaller testing region heights are possible. For example, testing region heights ranging from about 25 µm to about 100 µm are preferred in some embodiments of the present invention.

The vent 22 extends from the sample testing region 34 toward the rear face 36 of the optical format 10. According to some embodiments of the present invention, the vent 22 serves to ensure capillary movement of sample from the sample collection opening 18 toward the sample testing region 34. The vent 22 of the embodiment shown in FIGS. 1-4 has a rectangular cross-section with a height $h_v$, a width $w_v$, and a length $l_v$. According to one embodiment of the present invention, the height $h_v$ of the vent is approximately 100 µm, the width $w_v$ of the vent is approximately 500 µm, and the length $l_v$ of the vent is approximately 400 µm. Other vent dimensions are contemplated in other embodiments of the present invention. For example, vent heights ranging from about 50 µm to about 200 µm, vent widths ranging from about 50 µm to about 200 µm, and vent lengths ranging from about 50 µm to about 500 µm are preferred in some embodiments of the present invention. In addition to increasing capillary force in the capillary gap of the sample testing region 34, the vent 22 may provide an area for sample overfill.

The platform 28 may be provided with a reagent thereon designed to react with the sample in the sample testing region 34. Reagent may be placed on the platform via pump depositing, or by methods such as printing, pin deposition, or ink jetting. A reagent may be retained on the platform 28 by oven-drying before assembly of the optical format 10. According to one embodiment of the present invention, a reagent is deposited on the platform 28 before the optical format members are joined together. In this embodiment of the invention, the platform 28 keeps the reagent from spreading beyond the platform 28 or the sample testing region 34. Further, when a reagent is uniformly deposited on the platform 28, a uniform thickness of reagent and a uniform reaction area are achieved. According to some embodiments of the present invention, reagent combines with a sample within the sample testing region 34 to result in a colormetric reaction. The resulting color may be analyzed using diffuse reflectance or transmission through the sample.

According to some embodiments of the present invention, adhesive is provided between the format members to glue the first format member 12 to the second format member 14. In one embodiment of the present invention, heat-activated optically-clear adhesive is coated onto the inner surface of one or both of the format members for adhesion of the format members.

According to some embodiments of the present invention, top and bottom optical format members both comprise optically clear material. These embodiments may be used for optical transmission or diffuse reflectance analysis. Alternatively, one of the optical format members may comprise optically reflective material. Embodiments using optically reflecting material may be used in optical analysis based on diffused or reflected light from a sample.

The formats and methods of the present invention allow for the efficient construction of small and reliable optical formats. As shown in FIG. 1, a format has a format length $l_f$, a format width $w_f$, and a format height $h_f$. According to one embodiment of the present invention, the format length is approximately 3.85 mm, the format width is approximately 3 mm, and the format height is approximately 1 mm. Formats having other dimensions may be preferred in some embodiments of the present invention. For example, format lengths ranging from about 3.00 mm to about 12.5 mm, format widths ranging from about 2.00 mm to about 5.00 mm, and format heights ranging from about 0.50 mm to about 3.00 mm are preferred in some embodiments of the present invention. Optical formats according to the present invention may be designed for handling a wide range of sample fluid volumes. For example, sample volumes from about 5 nl to about 1000 nl are contemplated in some embodiments of the present invention. While the present invention has been described with reference to one or more particular embodiments, those skilled in the art will recognize that many changes may be made thereto without departing from the spirit and scope of the present invention.

For example, while the present invention has been generally described as directed to medical applications it is to be understood that other optical fluid testing applications might employ the principles of the invention. Each of these embodiments and obvious variations thereof is contemplated as falling within the spirit and scope of the claimed invention, which is set forth in the following claims.

What is claimed is:

1. A format for optical testing of a sample comprising:
    a first format member comprising a first inner surface and a platform extending a distance from said inner surface;
    a second format member comprising a second inner surface and a well disposed within said second inner surface, said well having a predetermined volume and shaped to accept said platform of said first format member within said well, said platform filling a significant portion of said predetermined volume such that said well and said platform define a sample testing region having a sample testing region volume significantly less than said predetermined volume and having a predetermined sample testing region height;
    a sample fill nose disposed within said second format member and extending from a sample collection opening at a first end of said sample fill nose to intersect with said well at a second end of said sample fill nose; and
    a vent disposed within said second format member and extending along said second inner surface from a vent opening at a first end of said vent to intersect with said well at a second end of said vent,
    wherein said sample fill nose has a sample fill nose cross-section and said vent has a vent cross-section different from said sample fill nose cross-section, said vent configured to receive sample overfill from said sample testing region via said second end of said vent.

2. The format of claim 1 wherein said second end of said vent intersects with said well at an area approximately opposing the intersection of said second end of said sample fill nose with said well.

3. The format of claim 1 wherein said platform extends from said first inner surface to a platform height and wherein said well extends within said second format member to a well depth greater than said platform height, the difference of said well depth and said platform height defining said sample testing region height.

4. The format of claim 1 wherein said platform is provided with a reagent thereon for reacting with said sample.

5. The format of claim 3 wherein said sample fill nose has a fill a fill nose volume greater than said sample testing region volume.

6. A format for optical testing of a sample comprising:
    a first format member comprising a first inner surface and a platform extending to a platform height from said inner surface;
    a second format member comprising a second inner surface and a well disposed within said second inner surface and extending a well depth below said second inner surface, said well having a first volume and shaped to accept said platform of said first format member within said well, said platform filling a significant portion of said first volume of said well thereby forming a sample testing region having a predetermined sampling volume that is significantly less than said first volume;
    a sample fill nose extending from a sample collection opening at a first end of said sample fill nose to said well at a second end of said sample fill nose; and
    a vent extending from a vent opening at a first end of said to said well at a second end of said vent,
    wherein said sample fill nose has a sample fill nose cross-section and said vent has a vent cross-section different from said sample fill nose cross-section, said vent configured to receive sample overfill from said sample testing region via said second end of said vent.

7. The format of claim 6 wherein said platform is cylindrical and has a platform diameter and said well is cylindrical and has a well diameter greater than said platform diameter.

8. The format of claim 6 wherein said sample fill nose is adapted to transport a volume of said sample from said sample collection opening to said sample testing region via capillary action.

9. The format of claim 8 wherein said volume of said sample is approximately 50 nl.

10. The format of claim 8 wherein said volume of said sample is within the range of from approximately 5 nl to approximately 1000 nl.

11. The format of claim 7 wherein said vent opening is provided on an opposite side of said format from said sample collection opening.

12. A method of manufacturing a format for optical testing, the method comprising the acts of:
    providing a first format member comprising a first inner surface and a platform extending to a platform height above said first inner surface;
    providing a second format member comprising:
        a) a second inner surface and a well disposed within said second inner surface and extending to a well depth below said second inner surface, said well depth being greater than said platform height, said well having a first volume;
        b) a sample fill nose notch having a first width, said sample fill nose notch terminating at said well; and
        c) a vent notch having a second width different that said first width, said vent notch terminating at said well; and
    joining said first format member to said second format member by inserting said platform of said first format member into said well of said second format member, said platform filling a significant portion of said first volume of said well thereby forming a sample testing region having a sample region volume that is significantly less than said first volume, wherein said vent notch is configured to receive sample overfill from said sample testing region.

13. The method of claim 12 further comprising applying a testing reagent to said platform.

14. The method of claim 12 wherein said sample fill nose notch approximately opposes said vent notch across said well.

15. The method of claim 12 further comprising providing adhesive on one or both of said first and second format members.

16. The method of claim 12 wherein said vent notch has a rectangular cross-section.

17. The method of claim 12 wherein said fill nose notch has a rectangular cross-section.

18. A format for optical testing of a sample comprising:

a first format member comprising a first inner surface and a platform extending a distance from said inner surface in a direction substantially perpendicular to said inner surface;

a second format member comprising a second inner surface and a well disposed within said second inner surface, said well being shaped to accept said platform of said first format member within said well, said well and said platform defining a sample testing region having a first volume; and a sample fill nose disposed within said second format member and extending from a sample collection opening at a first end of said sample fill nose to intersect with said well at a second end of said sample fill nose, said sample fill nose having a second volume approximately equal to said first volume.

19. The format of claim 1 wherein said vent cross-section has a first area and said sample fill nose cross-section has a second area, said first area is greater than said second area.

20. The format of claim 8 wherein said vent cross-section has a first area and said sample fill nose cross-section has a second area, said first area is greater than said second area.

21. The method of claim 12 wherein said first width is greater than said second width.

22. The format of claim 1 wherein said platform extends in a direction substantially perpendicular to said inner surface.

\* \* \* \* \*

UNITED STATES PATENT AND TRADEMARK OFFICE
CERTIFICATE OF CORRECTION

| | | |
|---|---|---|
| PATENT NO. | : 8,226,904 B2 | Page 1 of 1 |
| APPLICATION NO. | : 10/576993 | |
| DATED | : July 24, 2012 | |
| INVENTOR(S) | : Andrew J. Dosmann | |

It is certified that error appears in the above-identified patent and that said Letters Patent is hereby corrected as shown below:

In column 5, line 58 (Claim 5, line 2), delete the duplicative term "a fill".

In column 6, line 9 (Claim 6, line 17), after the word "said" insert the word -- vent --.

In column 6, line 44 (Claim 12, line 14), replace the word "that" and replace with the word -- than --.

Signed and Sealed this
Thirteenth Day of November, 2012

David J. Kappos
*Director of the United States Patent and Trademark Office*